(12) United States Patent
Hermansson et al.

(10) Patent No.: US 7,402,202 B2
(45) Date of Patent: *Jul. 22, 2008

(54) METHOD FOR THE MANUFACTURING OF A POWDERED MATERIAL, THE POWDERED MATERIAL AND A CERAMIC MATERIAL MANUFACTURED THERE FROM

(75) Inventors: Leif Hermansson, Länna (SE); Håkan Engqvist, Knivsta (SE)

(73) Assignee: Doxa Aktiebolag, Uppsala (SE)

( * ) Notice: Subject to any disclaimer, the term of this patent is extended or adjusted under 35 U.S.C. 154(b) by 7 days.

This patent is subject to a terminal disclaimer.

(21) Appl. No.: 10/490,625

(22) PCT Filed: Aug. 21, 2002

(86) PCT No.: PCT/SE02/01480

§ 371 (c)(1),
(2), (4) Date: Mar. 25, 2004

(87) PCT Pub. No.: WO2004/037215

PCT Pub. Date: May 6, 2004

(65) Prior Publication Data

US 2004/0206272 A1    Oct. 21, 2004

(30) Foreign Application Priority Data

Sep. 26, 2001    (SE) .................................... 0103189

(51) Int. Cl.
*C09K 3/00* (2006.01)
*C04B 7/32* (2006.01)
(52) U.S. Cl. ........................................ 106/35; 106/692
(58) Field of Classification Search .................... 106/35, 106/692
See application file for complete search history.

(56) References Cited

U.S. PATENT DOCUMENTS 3,942,994 A * 3/1976 Murray et al. .............. 106/693
6,107,229 A * 8/2000 Luck et al. .................. 501/151
6,620,232 B1   9/2003 Kraft et al.

FOREIGN PATENT DOCUMENTS

| EP | 0559627 | 9/1993 |
|---|---|---|
| JP | 53-037488 | 4/1978 |
| SE | 463493 | 12/1990 |
| SE | 502987 | 8/1993 |
| SE | 514686 | 4/2000 |
| WO | WO 90/11066 | 10/1990 |
| WO | WO 00/21489 A1 | 4/2000 |
| WO | WO 00/71082 A1 | 11/2000 |
| WO | WO 01/76534 A1 | 10/2001 |

OTHER PUBLICATIONS

Database WPI, Week 198306, Derwent Publications, Ltd., London, GB; AN 1983-13228K & JP 57209871 A (Yoida S), Dec. 23, 1982, abstract.
Database WPI, Week 197646, Derwent Publications, Ltd., London, GB; AN 1976-86141X & JP 51 111828 A (Matsushita Electric Works LTD), Oct. 2, 1976, abstract.
English language abstract of JP 57-209871, Dec. 23, 1982.

* cited by examiner

*Primary Examiner*—Elizabeth D Wood
(74) *Attorney, Agent, or Firm*—Birch, Stewart, Kolasch & Birch, LLP

(57) ABSTRACT

Powdered material, the binder phase of which mainly consists of a cement-based system, which powdered material has the capacity following saturation with a liquid reacting with the binder phase to hydrate to a radiopaque and chemically bonded ceramic material. According to the invention, said binder phase mainly consists of $CaO \cdot Al_2O_3$ (ss) and/or $3CaO \cdot Al_2O_3$ (ss). The material also contains one or more heavy atom types with a density over 5 g/cm³. The invention also relates to a method for manufacturing the powdered material and the chemically bonded ceramic material formed from the powdered material, in which said binder phase has a mol ratio $Al_2O_3 \cdot 3H_2O$ (ss) to $3CaO \cdot Al_2O_3 \cdot 6H_2O$ (ss) of a maximum of 2:1.

54 Claims, No Drawings

METHOD FOR THE MANUFACTURING OF A POWDERED MATERIAL, THE POWDERED MATERIAL AND A CERAMIC MATERIAL MANUFACTURED THERE FROM

TECHNICAL FIELD

The present invention relates to a radiopaque and chemically bonded ceramic material, the binder phase of which consists mainly of a cement-based system. The invention also relates to a powdered material that has the capacity to form said ceramic material when it is saturated with a liquid reacting with the binder phase, and a method of manufacturing this powdered material. The invention has been developed primarily with a view to dental and orthopaedic purposes, but can also be applied in other application areas.

PRIOR ART AND PROBLEMS

The present invention relates to binding agent systems of the cement system type, in particular the system $CaO$—$Al_2O_3$—$(SiO_2)$—$H_2O$. Studies carried out according to the invention and earlier works (SE 463 493, SE 502 987 and SE 514 686) have produced results that indicate great potential for the system for strong and acid-resistant materials such as dental filling material. No other dental filling material existing today meets all the requirements in respect of biocompatibility, aesthetics and function that can be posed by patients and dental service staff.

A description is given below of the practical demands that should generally be made on a dental filling material. Good handling ability with simple applicability in a cavity, moulding that permits good modellability, hardening/solidification that is sufficiently rapid for filling work and provides serviceability directly following a visit to the dentist. Furthermore, high strength and corrosion resistance exceeding that of earlier filling materials, good biocompatibility, radiopacity for X-ray purposes, good aesthetics and safe handling for staff without any allergy-provoking or toxic additives in the material are required. Good long-term attributes as regards dimensional stability are also demanded.

In SE 463 493 it was described how a chemically bonded ceramic material, e.g. for dental purposes, can be caused to exhibit increased strength characteristics in that a powder body consisting of one or more hydraulic binding agents and possible ballast material is compacted at such a high external pressure and at so low a temperature that a well held-together raw compact is obtained without sintering reactions on compacting. The filling density in this raw compact has increased to at least 1.3 times the initial filling density, which is defined as the filling density attained through shaking, vibration and/or light packing of the loose powder into a container. The user of the material prepares the same by saturating the raw compact with a hydration liquid prior to application of the material or in situ in a cavity, e.g. a tooth cavity.

More recently it has been shown in SE 502 987 that for cement systems complete hydration (which was regarded as reducing the risk of dimensional changes) can take place if complete soaking and subsequent compaction of the cement system takes place with the aid of a specially designed stopper.

More recently still it has been shown in SE 514 686 that a cement system of the type referred to in SE 463 493 or SE 502 987 can be caused to exhibit dimensionally stable long-term attributes if the material includes one or more expansion-compensating additives.

Materials that are produced according to SE 463 493, SE 502 987 or SE 514 686 have certainly proved to satisfy most of the demands that can be made according to the above on dental filling material. However, it has proved to be the case that the aesthetics of the material suffer, in spite of a colour similar to natural tooth colour, due to the fact that the material is opaque, which means that the material does not have adequate optical attributes to appear natural. Natural tooth transmits light, especially enamel. The manner in which the light is diffused through the tooth is described as translucent, which is to be differentiated from transparent. A definition of a translucent material reads: "A material that reflects, transmits and absorbs light. Objects cannot be seen clearly through the material when the material is placed between the object and the observer." (Lemire, Burk, Color in dentistry, J.M. Ney Company (1975)). One method of measuring translucence is to determine the ratio between the quantity of reflected light with a white background and with a black background (ISO 9917). A material is described as translucent if it has opacity of between 35 and 90%, as opaque above 90% and transparent below 35%. Natural dentine has an opacity of approx. 70%, while natural enamel has an opacity of around 35%. The ability of a filling material to imitate the appearance of the natural tooth depends to a large extent on the material being translucent.

In the abstract to JP 57209871 it is stated that translucence can be attained in a material of Portland cement and water glass.

In JP 51111828, a method is described for the production of $3CaO.Al_2O_3.6H_2O$. In the method, the raw materials for the binder phase are mixed with a surplus of water for 1-20 hours, with gradual heating from room temperature to 100° C. It is stated that hydrated calcium aluminate in the form of $3CaO.Al_2O_3.6H_2O$ is formed thereby. This hydrated calcium aluminate is heated to between room temperature and 100° C. and compressed at the same time at 50-800 MPa for 10-60 minutes, possibly following the addition of further water, to form a ceramic that is then dried at 60-250° C. without the water of crystallization being evaporated. In the method described in JP 51111828, the mechanical compression of already hydrated material is thus executed.

A related problem is that of achieving radiopacity at the same time as translucence, the former being required in a filling material in order for it to be able to be distinguished clearly from natural tooth and the onset of decay respectively in X-raying. The problem is due to the fact that the X-ray contrast aids that are common nowadays, e.g. $ZrO_2$ and $SnO_2$, interfere with the translucence. Even in an orthopaedic context or other non-biological context it is often desirable to have radiopacity, even if the need for translucence does not exist in this case.

Yet another problem is that of achieving the highest possible mechanical strength and hardness in the ceramic material formed. It is also desirable here, especially in connection with dental purposes, primarily fillings, for hardness to develop rapidly. Increased chemical stability is also an aspect, in which the share of $Al^{3+}$ in the material influences stability. It is desirable for the quantity $Al^{3+}$ to be minimized.

ACCOUNT OF THE INVENTION

One object of the present invention is to provide a ceramic material of the type stated in the introduction, which material exhibits radiopacity, high mechanical strength and rapid hardness development. The material shall preferably exhibit translucence at the same time, at least if the material is intended for dental purposes. The invention also aims to provide a powdered material that has the capacity following saturation with a liquid reacting with the binder phase to hydrate to a chemically bonded ceramic material of the type intended according to the invention. The invention also aims to offer a method for the manufacture of such a powdered material. The invention also aims to offer a ceramic filler material.

The desired objects and others are achieved according to the invention in that the binder phase of the powdered material mainly consists of $CaO.Al_2O_3$ (ss) and/or $3CaO.Al_2O_3$ (ss) and in that the powdered material and thus the ceramic material contain an atom type with a density above 5 $g/cm^3$, expressed as the density of the element that corresponds to the atom type.

In product terms, this means that the binder phase of the ceramic material formed has a mol ratio $Al_2O_3.3H_2O$ (ss) to $3CaO.Al_2O_3.6H_2O$ (ss) of a maximum of 2:1, preferably of less than 1:5 and even more preferredly less than 1:10.

The designation (ss) here means "solid solution". As will be described in greater detail later, this means that the binder phase can, but does not have to, contain other atom types that are present in solid solution in the binder phase, these replacing Ca and/or Al in full or in part In the quantity ratios that are indicated, these other atom types are counted as Ca or Al.

The term binder phase is taken here to mean a cement content in the material, regardless of whether the powdered material or the hydrated ceramic product is in question.

In method terms, the object of the invention is achieved in that the method for the manufacture of the powdered material comprises the stages of:
a) Mixing raw materials for the binder phase containing Ca and Al in a ratio Ca:Al greater than or equal to 1:2.4, preferably greater than or equal to 1:2.2 and most preferredly greater than or equal to 1:2, but no greater than 3:2.
b) Physically reducing diffusion paths between atoms in the various raw materials,
c) Sintering the material at an increased temperature to form said binder phase, which consists mainly of $CaO.Al_2O_3$ (ss) and/or $3CaO.Al_2O_3$ (ss), the material in stage a) and/or following stage c being brought to contain one or more heavy atom types with a density of over 5 $g/cm^3$, expressed as the density for the element of the atom type.

On hydration, two final phases, $3CaO.Al_2O_3.6H_2O$ and $Al_2O_3.3H_2O$ will always be formed from conventional cement mixtures containing calcium aluminates of the phases $CaO.Al_2O_3$ and $CaO.2Al_2O_3$. The invention is based on the knowledge that $Al_2O_3.3H_2O$ is not desirable as it can have a detrimental effect on the mechanical properties of the ceramic product To have more than one phase also affects the refraction of light by the ceramic material, since $Al_2O_3.3H_2O$ and $3CaO.Al_2O_3.6H_2O$ have different refractive indices. It is therefore desirable to be able to manufacture a material that has only one phase, namely $3CaO.Al_2O_3.6H_2O$, in the hydrated state, or at least to be able to manufacture a material that has a minimized content of $Al_2O_3.3H_2O$. By using only $3CaO.Al_2O_3$ as the binder phase, the hydrated material can be controlled to contain only $3CaO.Al_2O_3.6H_2O$. $3CaO.Al_2O_3.6H_2O$ has a higher mechanical strength than $Al_2O_3.3H_2O$ and the refraction is also reduced, resulting in lower opacity, i.e. increased translucence. It is also the case that the hydration time is shortened, as fewer phases are formed, and that several stages in the hydration process are shorter. By instead using only $CaO.Al_2O_3$ as the binder phase, the hydrated material can be controlled to contain $3CaO.Al_2O_3.6H_2O$ to $Al_2O_3.3H_2O$ in the ratio 1:2, which signifies a considerably greater proportion of $3CaO.Al_2O_3.6H_2O$ than if conventional powder mixtures containing calcium aluminates of the phases $CaO.Al_2O_3$ and $CaO.2Al_2O_3$ are used. Naturally mixtures of $CaO.Al_2O_3$ and $3CaO.Al_2O_3$ can also be used for a reduced formation of $Al_2O_3.3H_2O$. However, the binder phase's content of $CaO.2Al_2O_3$ should be minimized and preferably omitted completely.

Yet another advantage of the ceramic material according to the invention is that it contains a lower proportion of Al ions than conventional calcium aluminate compositions, which ought to be an advantage in biological systems, especially in orthopaedic applications.

With a view to achieving radiopacity, the powdered material, and thus also the ceramic product, contains at least one heavy atom type with a density of over 5 $g/cm^3$, preferably Zr, La, Ta, Zn, Ba and/or Sr. It is preferred that this/these atom type(s) form part of one or more compounds that also contain fluoride.

According to one aspect of the invention, the powdered material and thus also the ceramic product contains in addition to the binder phase one or more additives that contain the heavy atom type or atom types and that have a refractive index in visible light that deviates by a maximum of 15%, preferably a maximum of 10% and even more preferredly a maximum of 5% from the refractive index of the binder phase when the binder phase is hydrated. It is preferred that the additive is a glass, i.e. amorphous phase, most preferredly a silicate glass.

Examples of additive materials that satisfy one or more of the stated requirements are: silicate glass, barium aluminium borosilicate glass, barium aluminium fluorosilicate glass, barium sulphate, barium fluoride, zirconium-zinc-strontium-borosilicate glass, apatite, fluorapatite and similar materials. In these materials barium can be exchanged for strontium and the materials can also contain fluoride. The additive materials can also have any morphology or form, including: spheres, regular or irregular forms, whiskers, plates or the like. Particles of the additive material should be smaller than 50 µm, preferably smaller than 20 µm and even more preferredly smaller than 10 µm. The size of the particles is measured by laser diffraction and calculated as the volume mean value D[4,3]. Additive materials of this type can be present in total quantities of at least 3% by volume, preferably at least 5% by volume and even more preferredly at least 10% by volume, but at most 55% by volume, preferably at most 50% by volume and even more preferredly at most 45% by volume in the powdered material.

According to the above, according to an alternative embodiment of the invention, the heavy atom type or atom types can instead be included in the actual binder phase in such a way that they replace Ca and go into the solid solution (ss) in the binder phase, or alternatively form a compound that is close chemically and/or structurally. Apart from Ca positions (where Ba, Sr etc. can replace Ca), solid solution (ss) in e.g. $3CaO.Al_2O_3.6H_2O$ is possible in $H_2O$ positions (where oxides of Si, Ti, Zr etc. or fluorides can replace $H_2O$) and in Al positions (where Fe, V, Sn, Bi and P etc. can replace Al), it being possible to influence properties apart from radiopacity, such as dimensional stability, chemical resistance etc. positively. To manufacture the binder phase, raw materials are preferably used in this case that contain a heavy atom type in the same group as Ca in the periodic system, suitably Ba and/or Sr, and in addition possibly fluoride. The advantage of this is that the actual binder phase is radiopaque, and that the atoms that provide radiopacity do not interfere with translucence.

The two variants can naturally also be combined, additives with a heavy atom type being mixed into the powdered material together with the binder phase, which binder phase also contains heavy atom type(s).

In the same way as Ba and/or Sr can be used to replace Ca in the binder phase, with a view to achieving radiopacity and translucence at the same time, silicon in the form of fine crystalline silica (microsilica) and/or Portland cement (OPC) can be caused to go into solid solution (ss) in the binder phase, with a view to achieving dimensional stability of the ceramic product.

Solid solution (ss) in e.g. $3CaO.Al_2O_3.6H_2O$ can be produced in such a way that the solid solutions—with increased radiopacity—are non-hydrating. In these cases, these can be used advantageously as an inert phase to analogue solid solutions that are hydrating. This considerably increases the degree of freedom as regards the choice of raw materials and manufacturing criteria.

The powdered material shall further satisfy the requirements indicated above for mouldability and durability, and be easy to handle in connection with its wetting and application in a cavity, e.g. a tooth cavity. The ceramic material formed should also, for dental applications, meet the demands made on such a material according to the above. It is especially preferred that the material exists in the form of a raw compact that has a degree of compaction of 40-80% by volume solid phase, preferably 50-70% by volume solid phase and even more preferredly 55-65% by volume solid phase prior to hydration, in a manner such as described in SE 463 493. However, the invention is also fully applicable in connection with a wet-moulded material that exists in powder form prior to hydration, such as the material described in SE 502 987. The material can also contain one or more expansion-compensating additives suitable for giving the ceramic material dimensionally stable long-term attributes, such as described in SE 514 686. It is generally the case that said binder phase consists at least chiefly of calcium aluminate cement However, the addition of one or more other cement binder phases to a total amount of less than 30% by volume can be used, preferably 1-20% by volume and even more preferredly 1-10% by volume. Admixtures of ordinary Portland cement (OPC cement) or fine crystalline silica, which according to the above can possibly be included in solid solution in the binder phase, are used advantageously. Furthermore, it is desirable for the material to have a hardness of at least 50 HV in the hydrated state, preferably at least 100 HV and even more preferredly at least 140 HV.

DETAILED DESCRIPTION OF THE INVENTION

According to one aspect of the invention, the binder phase of the powdered material consists up to at least 70% by weight, preferably at least 80% by weight and even more preferredly at least 90% by weight, of $CaO.Al_2O_3$ and/or $3CaO.Al_2O_3$ (ss).

According to another aspect of the invention, the binder phase of the powdered material consists mainly of $3CaO.Al_2O_3$ (ss), preferably up to at least 70% by weight, more preferredly at least 80% by weight and most preferredly at least 90% by weight. Alternatively, the binder phase of the powdered material consists mainly of $CaO.Al_2O_3$ (ss), preferably up to at least 70% by weight, more preferredly at least 80% by weight and most preferredly at least 90% by weight. All mixtures between these alternatives are also conceivable.

A first embodiment of the method for manufacturing the powdered material comprises the stages of:

a) Mixing raw materials for the binder phase containing Ca and Al in a ratio Ca:Al greater than or equal to 1:2.4, preferably greater than or equal to 1:2.2 and most preferredly greater than or equal to 1:2, but no greater than 3:2.

b) Mechanically reducing the diffusion paths between atoms in the various raw materials by pressurizing the raw materials, e.g. through cold isostatic pressing, at a pressure of 10-350 MPa, preferably 50-300 MPa and even more preferredly 150-250 MPa, to form a pressed powder body, following which the powder body is finely divided into granules, preferably of less than 1 mm, even more preferredly of less than 0.5 mm and most preferredly of less than 0.3 mm in size, c) Sintering the material at a temperature of at least 1200° C. to form said binder phase, which consists mainly of $CaO.Al_2O_3$ (ss) and/or $3CaO.Al_2O_3$ (ss), d) Grinding the material to a particle size of less than 80 µm, preferably less than 30 µm and even more preferredly less than 20 µm, e) Mixing the material with any additives, f) Pressing the material to form a raw compact with a degree of compaction of 40-80% by volume solid phase, preferably 50-70% by volume solid phase and even more preferredly 55-65% by volume solid phase.

According to one aspect of the method, said sintering is carried out at a minimum of 1250° C., preferably a minimum of 1275° C. and even more preferredly at least 1300° C. but at most 1600° C., preferably at most 1550° C. and even more preferredly at most 1360° C., for at least 2 hours, preferably at least 4 hours and even more preferredly at least 6 hours, said sintering preferably being preceded by drying at an increased temperature that is below the sintering temperature, e.g. at a temperature of around 1000° C.

A second embodiment of the method for manufacturing the powdered material comprises the stages of:

a) Mixing raw materials for the binder phase containing Ca and Al in a ratio Ca:Al greater than or equal to 1:2.4, preferably greater than or equal to 1:2.2 and most preferredly greater than or equal to 1:2, but no greater than 3:2.

b) Chemically reducing the diffusion paths between atoms in the various raw materials by mixing the raw materials with 2-10 times more water than powder raw material, which mixture is heated to 30-100° C. while stirring for 1-20 hours, preferably 2-5 hours, to form $3CaO.Al_2O_3.6H_2O$ in grain shape, following which any dissolved water is evaporated at a temperature lower than 250° C., preferably lower than 150° C., even more preferredly lower than 100° C. but at least 50° C., c) Sintering the material through heat treatment at a temperature of over 250° C., preferably over 500° C. and even more preferredly over 1000° C. for at least 15 minutes, preferably at least 1 hour, the water of crystallization evaporating and said binder phase being formed, which consists mainly of $CaO.Al_2O_3$ (ss) and/or $3CaO.Al_2O_3$ (ss), d) Grinding the material to a particle size of less than 80 µm, preferably less than 30 µm and even more preferredly less than 20 µm, e) Mixing the material with any additives, f) Pressing the material to form a raw compact with a degree of compaction of 40-80% by volume solid phase, preferably 50-70% by volume solid phase and even more preferredly 55-65% by volume solid phase.

According to one aspect of the method, regardless of the embodiment, said raw materials containing Ca and Al consist of at least one of the raw materials in the group that consists of powdered CaO, $CaCl_2$, $Ca(OH)_2$ and $CaCO_3$ and at least one of the raw materials in the group that consists of powdered $Al_2O_3$, $AlCl_3$, $Al_2O_3.H_2O$ and $Al(OH)_3$. In the event that it is desired to manufacture a binder phase that contains a heavy atom type in solid solution, the whole or parts of the raw materials containing Ca can be exchanged for Ba and/or Sr compound(s), e.g. BaO, $BaCl_2$, $BaO_2$, $Ba(OH)_2.8H_2O$, $BaF_2$, $BaH_2$, SrO, $SrCl_2$, $Sr(OH)_2.8H_2O$, $SrF_2$, $SrH_2O$ to 100%, preferably 20-50%, of the raw material containing Ca can thereby be exchanged for raw material containing Ba and/or Sr.

In the event that it is desired to manufacture a binder phase containing silicon and/or fluoride in solid solution, the raw materials can also contain fine crystalline silica (microsilica) and/or Portland cement (OPC) and/or fluorides of Na, Mg, Mn, Ca, Ba, Sr etc.

In the event that it is desired to manufacture a binder phase that contains metals such as iron, vanadium, titanium, zirconium, tin, bismuth in solid solution, the raw materials can also contain oxides, hydroxides or salts of these elements.

In the event that it is desired to manufacture a binder phase that contains phosphorus in solid solution, the raw materials can also contain Ca, Ba, Sr-phosphates and apatites including fluorapatite.

According to an aspect of the invention, it is preferred that the material, regardless of the embodiment, is ground in stage d and possibly screened so that the material has particle sizes of over 3 μm, preferably over 2 μm and even more preferredly over 1 μm and/or particle sizes under 300 nm, preferably under 200 nm. The particle size is measured by laser diffraction and the volume-weighted mean value is indicated (also called D[4,3]).

It is preferred from the translucence viewpoint that the raw materials for the binder phase have a high whiteness, the whiteness value preferably exceeding 70, preferably exceeding 74 according to ASTM E313. The content of transition metals in the powder mixture should for the same reason be under 0.5% by weight, preferably under 0.4% by weight.

The translucence can be improved further by a low level of porosity of the finished ceramic material, preferably a porosity level of less than 20%, even more preferredly of less than 10% and still more preferredly of less than 5%.

Thanks to the invention, the ceramic material formed can be caused to have a translucence corresponding to 35-90%, preferably 40-85% and even more preferredly 50-80% opacity. At the same time, a hardness of at least 50 HV, preferably at least 100 HV and even more preferredly 140 HV can be achieved.

To manufacture a filler material, the method for manufacture according to the second embodiment can be interrupted after stage b. A filler material of this kind is a ceramic product in itself according to the invention, which can be used as an additive in stage e. The stirring in stage b can possibly be controlled in this case so that the selected desired form can be achieved for the filler particles, or also the grains can be post-treated to the desired shape.

EXAMPLE 1

A series of experiments was carried out to study the effect of different process parameters in the manufacture of calcium aluminate, $3CaO.Al_2O_3$, and its influence on the material's translucence and mechanical properties, without regard to radiopacity.

Description of Raw Materials

Calcium aluminate of the phases $CaO.Al_2O_3$ and $CaO.2Al_2O_3$ forming part of e.g. calcium aluminate cement (Alcoa or alternatively Lafarge) CaO, $Ca(OH)_2$, $Al(OH)_3$, $Al_2O_3$ (Merck).

Examples a)-d) Below Describe
  a) Manufacture of $3CaO.Al_2O_3$ at high temperature from CaO and $Al_2O_3$
  b) Manufacture of $3CaO.Al_2O_3$ at low temperature from CaO and $A_2O_3$
  c) Manufacture of $3CaO.Al_2O_3$ at high temperature from $Ca(OH)_2$ and $Al(OH)_3$
  d) Manufacture of $3CaO.Al_2O_3$ at low temperature from $Ca(OH)_2$ and $Al(OH)_3$ The raw materials were mixed in such proportions that the mol ratio Ca:Al was 3:2.

Following mixing, the powder or granules were subjected to cold isostatic pressing in examples a)-d) at 250 MPa for a green body. Following pressing, the green bodies were ground into small granules. The powder mixtures in examples a)-d) were then sintered according to the following cycles:
  a) 1000° C. for 1 hour followed by 1480° C. for 8 hours then cooling to room temperature for 1 hour.
  b) 1000° C. for 1 hour followed by 1350° C. for 12 hours then cooling to room temperature for 1 hour.
  c) 1000° C. for 1 hour followed by 1480° C. for 4 hours then cooling to room temperature for 1 hour.
  d) 1000° C. for 1 hour followed by 1350° C. for 6 hours then cooling to room temperature for 1 hour.

Verification (X-ray diffraction) of the resulting phase composition in examples a-d) following sintering showed that all the original powder has been converted to $3CaO.Al_2O_3$.

The powders in examples a-d) were ground in a ball mill with inert grinding balls of silicon nitride with a filling level of 35%. Isopropanol was used as the grinding liquid. Following grinding, all the powder had a grain size of less than 20 μm. Following evaporation of the solvent, cylindrical raw compacts were made with a diameter of 10 mm and a height of 1 mm, which were wetted with water. The material was then kept moist at 37° C. for a week prior to measurements of translucence. The measurements of translucence were carried out according to ISO 9917 (100 means opaque and 35 to 90 means translucence). The hardness (Vickers method) of the material was measured after one week. The material was compared with a calcium aluminate cement containing the phases $CaO.Al_2O_3$ and $CaO.2Al_2O_3$ LaFarge). The phase composition following hydration was also verified (X-ray diffraction (XRD)). The results are shown in Table 1.

TABLE 1

| Sample designation | Hardness $HV_{0.1}$ | Opacity (%) ($C_{0.70}$) | Phase composition (XRD) |
| --- | --- | --- | --- |
| Reference | 130 | 73 | $Al_2O_3.3H_2O$ and $3CaO.Al_2O_3.6H_2O$ |
| A | 275 | 39 | $3CaO.Al_2O_3.6H_2O$ |
| B | 290 | 43 | $3CaO.Al_2O_3.6H_2O$ |
| C | 282 | 40 | $3CaO.Al_2O_3.6H_2O$ |
| D | 295 | 44 | $3CaO.Al_2O_3.6H_2O$ |

The results show that a material with increased hardness and improved translucence can be obtained by manufacturing the raw material for the material in a controlled manner with controlled phase composition.

EXAMPLE 2

A series of experiments was carried out to study the effect of different process parameters in the manufacture of calcium aluminate, $CaO.Al_2O_3$, and its influence on the material's translucence and mechanical properties, without regard to radiopacity.

Description of Raw Materials

Calcium aluminate of the phases $CaO.Al_2O_3$ and $CaO.2Al_2O_3$ forming part of e.g. calcium aluminate cement (Alcoa or alternatively Lafarge) CaO, $Ca(OH)_2$, $Al(OH)_3$, $Al_2O_3$ (Merck).

Examples a)-d) Below Describe
 a) Manufacture of $CaO.Al_2O_3$ at high temperature from CaO and $Al_2O_3$
 b) Manufacture of $CaO.Al_2O_3$ at low temperature from CaO and $Al_2O_3$
 c) Manufacture of $CaO.Al_2O_3$ at high temperature from $Ca(OH)_2$ and $Al(OH)_3$
 d) Manufacture of $CaO.Al_2O_3$ at low temperature from $Ca(OH)_2$ and $Al(OH)_3$ The raw materials were mixed in such proportions that the mol ratio Ca:Al is 1:2.

Following mixing, the powders or granules were subjected to cold isostatic pressing in examples a)-d) at 250 MPa to a green body. Following pressing, the green bodies were ground into small granules. The powder mixtures in examples a)-d) were then sintered according to the following cycles:
 e) 1000° C. for 1 hour followed by 1480° C. for 8 hours then cooling to room temperature for 1 hour.
 f) 1000° C. for 1 hour followed by 1350° C. for 12 hours then cooling to room temperature for 1 hour.
 g) 1000° C. for 1 hour followed by 1480° C. for 4 hours then cooling to room temperature for 1 hour.
 h) 1000° C. for 1 hour followed by 1350° C. for 6 hours then cooling to room temperature for 1 hour.

Verification (X-ray diffraction) of the resulting phase composition in examples a-d) following sintering showed that all the original powder has been converted to $CaO.Al_2O_3$.

The powders in examples a-d) were ground in a ball mill with inert grinding balls of silicon nitride with a filling level of 35%. Isopropanol was used as the grinding liquid. Following grinding, all the powder had a grain size of less than 20 µm. Following evaporation of the solvent, cylindrical sample bodies were made with a diameter of 10 mm and a height of 1 mm, which were wetted with water. The material was then kept moist at 37° C. for a week prior to measurements of translucence. The measurements of translucence were carried out according to ISO 9917 (100 means opaque and 35 to 90 means translucence). The hardness (Vickers method) of the material was measured after one week. The materials were compared with a calcium aluminate cement containing the phases $CaO.Al_2O_3$ and $CaO.2Al_2O_3$ (LaFarge) with the mol ratio 1:1. The phase composition following hydration was also verified (X-ray diffraction (XRD)). The results are shown in Table 2.

TABLE 2

| Sample designation | Hardness $HV_{0.1}$ | Opacity (%) ($C_{0.70}$) | Phase composition (XRD), $Al_2O_3.3H_2O:3CaO.Al_2O_3.6H_2O$ |
|---|---|---|---|
| Reference | 130 | 73 | 7:2 |
| A | 175 | 50 | 2:1 |
| B | 192 | 49 | 2:1 |
| C | 174 | 54 | 2:1 |
| D | 180 | 53 | 2:1 |

The results show that a material with increased hardness and improved translucence can be obtained by manufacturing the raw material for the material in a controlled manner with controlled composition of the binder phase.

EXAMPLE 3

A series of experiments was carried out to manufacture calcium aluminate with a solid solution of Ba and Sr ($3CaO.Al_2O_3$ (ss)) and its influence on the material's radiopacity.

Description of Raw Materials

Calcium aluminate of the phases $CaO.Al_2O_3$ and $CaO.2Al_2O_3$ forming part of e.g. calcium aluminate cement (Alcoa or alternatively LaFarge) CaO, BaO, SrO, $Al_2O_3$ (Merck).

Examples a)-b) Below Describe
 a) Manufacture of $3CaO.Al_2O_3$ (ss) from CaO, BaO and $Al_2O_3$
 b) Manufacture of $3CaO.Al_2O_3$ (ss) from CaO, SrO and $Al_2O_3$ The raw materials were mixed in such proportions that the mol ratio (Ca, Ba):Al in a) was 3:2 with the mol ratio Ca:Ba 2:1 and (Ca, Sr):Al in b) was 3:2 with the mol ratio Ca:Sr 1:1.

The powder mixtures or granules were mixed with 1 part powder and 5 parts water with stirring and heating to 75° C. The water and the powder were mixed for 6 hours. Phase analysis of the powder formed showed that it consisted completely of $3CaO.Al_2O_3.6H_2O$ (ss). This powder was heated up in an oven to 1000° C. for 2 hours. Verification (X-ray diffraction) of the resulting phase composition in examples a-b) following heating showed that all the original powder has been converted to $3CaO.Al_2O_3$ (ss).

The powders in examples a-b) were ground in a ball mill with inert grinding balls of silicon nitride with a filling level of 35%. Isopropanol was used as the grinding liquid. Following grinding, all the powder had a grain size of less than 20 µm. Following evaporation of the solvent, cylindrical raw compacts were made with a diameter of 10 mm and a height of 1 mm, which were wetted with water. The material was then kept moist at 37° C. for a week prior to measurements of radiopacity. The measurements of radiopacity were carried out according to ANSI/ADA Specification No. 27 (1 mm sample body as opaque as 2 mm Al).

The material was compared with a calcium aluminate cement containing the phases $CaO.Al_2O_3$ and $CaO.2Al_2O_3$ (LaFarge). The results are shown in Table 3.

TABLE 3

| Sample designation | Radiopacity |
|---|---|
| Reference | No |
| A | Yes |
| B | Yes |

The results show that a radiopaque material consisting of only the binder phase can be obtained using the method according to the invention.

EXAMPLE 4

A series of experiments was carried out to manufacture calcium aluminate with a solid solution ($3CaO.Al_2O_3$ (ss)) and its influence on the material's radiopacity.

Description of Raw Materials

Calcium aluminate of the phases $CaO.Al_2O_3$ and $CaO.2Al_2O_3$ forming part of e.g. calcium aluminate cement (Alcoa or alternatively Lafarge) CaO, $CaF_2$, BaO, SrO, $Fe_2O_3$, $Al_2O_3$ (Merck).

Examples a)-c) Below Describe e) Manufacture of $3CaO.Al_2O_3$ (ss) from CaO, BaO and $Al_2O_3$
f) Manufacture of $3CaO.Al_2O_3$ (ss) from CaO, SrO and $Al_2O_3$
g) Manufacture of $3CaO.Al_2O_3$ (ss) from CaO, SrO, $Fe_2O_3$ and $Al_2O_3$ The raw materials in the examples were mixed according to the mol ratios:

a) (Ca, Ba):Al as 3:2 with the mol ratio Ca:Ba 2:1
b) (Ca, Sr):Al as 3:2 with the mol ratio Ca:Sr 1:1
c) (Ca, Sr):(Al:Fe) as 3:2 with the mol ratios Ca:Sr 1:1 and A:Fe 5:1

Following mixing, the powder or granules were subjected to cold isostatic pressing in examples a)-c) at 250 MPa for a green body. Following pressing, the green bodies were ground into small granules. The powder mixtures in examples a)-c) were then sintered according to the following cycle: 1000° C. for 1 hour followed by 1480° C. for 8 hours then cooling to room temperature for 1 hour.

Verification (X-ray diffraction) of the resulting phase composition in examples a-c) following sintering showed that all the original powder has been converted to $3CaO.Al_2O_3$ (ss).

The powders in examples a-c) were ground in a ball mill with inert grinding balls of silicon nitride with a filling level of 35%. Isopropanol was used as the grinding liquid. Following grinding, all the powder had a grain size of less than 20 μm. Following evaporation of the solvent, cylindrical raw compacts were made with a diameter of 10 mm and a height of 1 mm, which were wetted with water. The material was then kept moist at 37° C. for a week prior to measurements of radiopacity. The measurements of radiopacity were carried out according to ANSI/ADA Specification No. 27 (1 mm sample body as opaque as 2 mm Al). The material was compared with a calcium aluminate cement containing the phases $CaO.Al_2O_3$ and $CaO.2Al_2O_3$ (LaFarge). The results are shown in Table 4.

TABLE 4

| Sample designation | Radiopacity |
| --- | --- |
| Reference | No |
| A | Yes |
| B | Yes |
| C | Yes |

The results show that a radiopaque material consisting of only the binder phase can be obtained using the method according to the invention.

EXAMPLE 5

Experiments were carried out to study the effect of the phase composition of the binder phase on the development of hardness with time for the material, without regard to radiopacity.

Description of Raw Materials

Calcium aluminate of the phases $CaO.Al_2O_3$ and $CaO.2Al_2O_3$ forming part of e.g. calcium aluminate cement (Alcoa or alternatively Lafarge). Calcium aluminate cement of the phase $3CaO.Al_2O_3$ manufactured according to Example 1 and calcium aluminate of the phase $CaO.Al_2O_3$ manufactured according to Example 2.

Examples a)-c) Below Describe a) The hardness as a function of time for calcium aluminate consisting of the phases $CaO.Al_2O_3$ and $CaO.2Al_2O_3$ (reference)
b) The hardness as a function of time for calcium aluminate consisting of the phase $CaO.Al_2O_3$
c) The hardness as a function of time for calcium aluminate consisting of the phase $3CaO.Al_2O_3$.

The powders or granules in examples a-c) were ground in a ball mill with inert grinding balls of silicon nitride with a filling level of 35%. Isopropanol was used as the grinding liquid. Following grinding, all the powder had a grain size of less than 20 μm. Following evaporation of the solvent, cylindrical sample bodies were made with a diameter of 10 mm and a height of 1 mm, which were wetted with water. The material was then kept moist at 37° C. for a week between measurements of hardness (Vickers method load 100 g). Measurements were carried out after 1, 2, 4, 8 and 16 days. The results are shown in Table 5.

TABLE 5

| Material | Hardness 1 day | Hardness 2 days | Hardness 4 days | Hardness 8 days | Hardness 16 days |
| --- | --- | --- | --- | --- | --- |
| A | 83 | 98 | 117 | 127 | 141 |
| B | 110 | 132 | 150 | 175 | 180 |
| C | 160 | 200 | 230 | 281 | 285 |

The results show that the hardness is developed more rapidly with time due to the fact that the raw material for the material was manufactured in a controlled manner with controlled composition of the binder phase.

EXAMPLE 6

A series of experiments was carried out to manufacture inert filler particles with solid solution ($3CaO.Al_2O_3.3SiO_2$ (ss)) and to study their influence on the material's radiopacity.

Description of Raw Materials

Calcium aluminate of the phases $CaO.Al_2O_3$ and $CaO.2Al_2O_3$ forming part of e.g. calcium aluminate cement (Alcoa or alternatively Lafarge) CaO, $CaF_2$, $SiO_2$, SrO, $Fe_2O_3$, $Al_2O_3$ (Merck).

The raw materials were mixed according to the mol ratios (Ca, Sr):(Al, Fe):(Si) 3:2:3 with the mol ratio Ca:Sr 1:1, Al:Fe 5:1 and $CaO:CaF_2$ 10:1.

Following mixing, the powder or granules were subjected to cold isostatic pressing at 250 MPa for a green body. Following pressing, the green bodies were ground into small granules. The powder mixture was then sintered according to the following cycle: 1000° C. for 1 hour followed by 1480° C. for 8 hours then cooling to room temperature for 1 hour.

Verification (X-ray diffraction) of the resulting phase composition in examples a-c) following sintering showed that all the original powder has been converted to $3CaO.Al_2O_3SiO_2$ (ss).

The powder was ground together with 70% by volume binder phase consisting of $3CaO.Al_2O_3$, manufactured according to EXAMPLE 1, in a ball mill with inert grinding balls of silicon nitride with a filling level of 35%. Isopropanol was used as the grinding liquid. Following grinding, all the powder had a grain size of less than 20 μm. Following evaporation of the solvent, cylindrical raw compacts were made with a diameter of 10 mm and a height of 1 mm, which were wetted with water. The material was then kept moist at 37° C.

for a week prior to measurements of radiopacity. The measurements of radiopacity were carried out according to ANSI/ADA Specification No. 27 (1 mm sample body as opaque as 2 mm Al). The material was compared with a calcium aluminate cement containing the phases $CaO.Al_2O_3$ and $CaO.2Al_2O_3$ (LaFarge). The results are shown in Table 6.

TABLE 6

| Sample designation | Radiopacity |
|---|---|
| Reference | No |
| Material | Yes |

The results show that a radiopaque material can be obtained by causing the powdered material according to the invention to contain inert particles.

The invention is not restricted to the embodiments described, but can be varied within the scope of the claims.

The invention claimed is:

1. Method for the manufacture of a powdered material, the binder phase of which comprises a cement-based system, which powdered material has the capacity following saturation with a liquid reacting with the binder phase to hydrate to a radiopaque and chemically bonded ceramic material, characterized by the stages of:
   a) mixing raw materials for the binder phase containing Ca and Al in ratio Ca:Al greater than or equal to 1:2.4, but no greater than 3:2,
   b) physically reducing diffusions paths between atoms in the various raw materials,
   c) sintering the material at an increased temperature to form said binder phase, which comprises $CaO.Al_2O_3$ (ss) and/or $3CaO.Al_2O_3$ (ss);
   the material in stage a and/or following stage c being brought to contain 10-55% by volume of one or more additive consisting of glass, said additive containing a non-trace amount of one or more element with a density over 5 $g/cm^3$, expressed as the density of the element, and
   wherein said one or more element becomes present in solid solution (ss) in the binder phase, and fully or partly replaces the calcium and/or aluminium atoms in the binder phase.

2. Method according to claim 1, characterized by, following stage c, a stage:
   d) the material is ground to a particle size of less than 80 μm.

3. Method according to one of claims 1 or 2, characterized by, following stage c or d, a stage:
   c) the material is mixed with glass additives containing the non-trace amount of one or more element having a density over 5 $g/cm^3$ and that have a refractive index in visible light that deviates by at most 15% from the refractive index of the binder phase when the binder phase is hydrated.

4. A powdered material, the binder phase comprising a cement-based system, which powdered material following saturation with a liquid reacting with the binder phase hydrates to a radiopaque and chemically bonded ceramic material, wherein
   said binder phase comprises $CaO.Al_2O_3$ and/or $3CaO.Al_2O_3$ and the powdered material contains one or more element with a density over 5 $g/cm^3$, expressed as the density for the element,
   said powdered material contains 10-55% by volume of one or more additive consisting of glass, said additive containing a non-trace amount of said one or more element, and
   said one or more element is present in solid solution (ss) in the binder phase, and fully or partly replaces the calcium and/or aluminium atoms in the binder phase.

5. The powdered material according to claim 4, wherein said binder phase comprises up to at least 70% by weight of $CaO.Al_2O_3$ and/or $3CaO.Al_2O_3$.

6. The powdered material according to claim 4, wherein said one or more element consists of one or more atoms in the group that consists of V, Fe, Zr, La, Bi, Sn, Ta, Zn, Ba and/or Sr.

7. The powdered material, according to claim 4, wherein said one or more glass additives have a refractive index in visible light that deviates by at most 15%, from the refractive index of the binder phase when the binder phase is hydrated.

8. The powdered material according to claim 4, wherein said additives consist of a silicate glass.

9. The powdered material according to claim 4, wherein said one or more element consists of one or more element in group 2 in the periodic system.

10. The powdered material according to claim 9, wherein the one or more element consists of Ba and/or Sr.

11. The powdered material according to claim 4, wherein silicon and/or fluoride are present in solid solution (ss) in the binder phase.

12. The powdered material according to claim 4, wherein silicon and/or fluoride are present in a raw material that forms said binder phase in the form of fine crystalline silica and/or Portland cement and/or fluorides of Na, Mg, Mn, Ca, Sr or Ba.

13. The powdered material according to claim 4, wherein iron and/or phosphorus are present in solid solution (ss) in the binder phase.

14. The powdered material according to claim 4, wherein iron and/or phosphorus are present in a raw material that forms said binder phase in the form of iron oxides, iron hydroxides or salt of iron and/or phosphorus in the form of phosphates of Ca, Ba, Sr or as apatites.

15. The powdered material according to claim 14, wherein the apatite is fluorapatite.

16. The powdered material according to claim 4, wherein it contains non-hydrating inert material.

17. The powdered material according to claim 16, wherein the non-hydrating inert material is of the type $3CaO.Al_2O_3.X$ (ss), in which X consists of an oxide or fluoride.

18. The powdered material according to claim 4, wherein it is present in the form of a raw compact that has a degree of compaction of 40-80% by volume solid phase.

19. The powdered material according to claim 4, wherein it is present in loose powder form or in the form of granules.

20. A method for the manufacture of a powdered material, the binder phase comprising a cement-based system, which powdered material following saturation with a liquid reacting with the binder phase hydrates to a radiopaque and chemically bonded ceramic material, characterized by the stages of:
   a) mixing raw materials for the binder phase containing Ca and Al in ratio Ca:Al greater than or equal to 1:2.4, and bringing said material to comprise one or more element with a density over 5 $g/cm^3$, expressed as the density of the element, but not greater than 3.2, and
   b) physically reducing diffusion paths between atoms in the various raw materials, wherein said material is brought to contain 10-55% by volume of one or more additive consisting of glass, said additive containing a non-trace amount of said one or more element, and said one or more element becomes present in solid solution (ss) in the binder phase, and fully or partly replaces the calcium and/or aluminium atoms in the binder phase.

21. The method according to claim 20, wherein said diffusion paths are reduced mechanically or chemically.

22. The method according to claim 20, wherein the diffusion paths are reduced mechanically in stage b, stage b including pressurizing of the raw material at a pressure of 10-350 MPa to form a pressed powder body, following which the powder body is finely divided into granules of less than 1 mm in size.

23. The method according to claim 22, wherein the diffusion paths are reduced mechanically in stage b, stage b including pressurizing of the raw material at a pressure of 150-250 MPa to form a pressed powder body, following which the powder body is finely divided into granules of less than 0.3 mm in size.

24. The method according to claim 22, wherein the pressurizing in stage b is performed by cold isostatic pressing.

25. The method according to claim 17, wherein said sintering in stage c is executed at least 1200° C., but at most 1600° C. for at least 2 hours.

26. The method according to claim 25, wherein said sintering in stage c is executed at least 1300° C., but at most: 1360° C., for at least 6 hours, said sintering being preceded by drying at an increased temperature below the sintering temperature.

27. The method according to claim 20, wherein the diffusion paths are reduced chemically in stage b, stage b including mixing of the raw materials with 2-10 times more water than powdered raw material, which mixture is heated to 30-100° C. with stirring for 1-20 hours, to form $3CaO.Al_2O_3.6H_2O$, following which any dissolved water is evaporated at a temperature lower than 250° C., but at least 50° C.

28. The method according to claim 27, wherein said sintering in stage c is executed at a temperature above 250° C., for at least 15 minutes, whereby water of crystallization is removed by evaporation.

29. The method according to claim 28, wherein said sintering in stage c is executed at a temperature above 1000° C. for at least 1 hour, whereby water of crystallization is removed by evaporation.

30. The method according to claim 20, wherein said raw materials containing Ca and Al in stage a consist of at least one of the raw materials in the group that consists of powdered CaO, $CaCl_2$, $Ca(OH)_2$ and $CaCO_3$ and at least one of the raw material in the group that consists of powdered $Al_2O_3$, $Al_2O_3.H_2O$, $AlCl_3$ and $Al(OH)_3$.

31. The method according to claim 20, wherein said one or more element consists of one or more element in the group that consists of V, Fe, Zr, La, Bi, Sn, Ta, Zn, Ba and/or Sr.

32. The method according to claim 31 wherein said one or more element with a density over 5 $g/cm^3$, expressed as the density of the element, is also added to the binder phase after a sintering step c.

33. The method according to claim 20, wherein raw materials in stage a also contain fine crystalline silica (microsilica) and/or Portland cement (OPC).

34. The method according to claim 17, wherein, following stage c, a stage:
c) the material is ground to a particle size of less than 80 μm.

35. The method according claim 17, wherein, following stage c, a stage:
d) the material is mixed with said glass additives which additives have a refractive index in visible light that deviates by at most 15% from the refractive index of the binder phase when the binder phase is hydrated.

36. The method according to claim 20, wherein said glass is a silicate glass.

37. The method according to claim 34, wherein, following stage c, a stage:
e) the material is mixed with said glass additives that have a refractive index in visible light that deviates by at most 15% from the refractive index of the binder phase when the binder phase is hydrated.

38. The method according to claim 35, wherein, following stage d, a stage:
e) the material is pressed to a raw compact with a degree of compaction of 40-80% by volume solid phase.

39. The method according to claim 37, wherein, following stage e, a stage:
f) the material is pressed to a raw compact with a degree of compaction of 40-80% by volume solid phase.

40. A radiopaque and chemically bonded ceramic material based on the powdered material defined in claim 4, in hydrated form, the binder phase comprising a cement-based system, suitable for dental purposes, wherein
said binder phase comprises $Al_2O_3.3H_2O$ and $3CaO.Al_2O_3.6H_2O$,
said material also contains one or more element with a density over 5 $g/cm^3$, expressed as the density of the element, and
said one or more element is present in solid solution (ss) in the binder phase, and fully or partly replaces the calcium and/or aluminium atoms in the binder phase.

41. The radiopaque and ceramic material according to claim 40, wherein it has a hardness of at least 50 HV.

42. The radiopaque and ceramic material according to claim 40, wherein it is a filler material in particle form.

43. The radiopaque and ceramic material according to claim 40, wherein said binder phase has a mol ratio $Al_2O_3.3H_2O$ to $3CaO.Al_2O_3.6H_2O$ of a maximum of 2:1.

44. The method according to claim 4, wherein 20-50% of the calcium and/or aluminum atoms in the raw material is exchanged for one or more element in group 2 in the periodic system.

45. The method according to 44, wherein said one or more element in group 2 in the periodic system is Ba and/or Sr.

46. The method according to claim 20, wherein the material formed in step b, in a further step c, is sintered at an increased temperature, whereby the one or more element with a density over 5 $g/cm^3$ fully or partly replaces the calcium and/or aluminum atoms of the binder phase and goes into the solid solution (ss) in the binder phase.

47. The method according to claim 46, wherein said binder phase comprises $CaO.Al_2O_3$ and/or $3CaO.Al_2O_3$.

48. The method according to claim 1, wherein the step a of mixing the raw materials for the binder phase containing Ca and Al in the ratio Ca:Al is greater than or equal to 1:2.2 but no greater than 3:2.

49. The method according to claim 1, wherein the step a of mixing the raw materials for the binder phase containing Ca and Al in the ratio Ca:Al is greater than or equal to 1:2 but no greater than 3:2.

50. The method according to claim 2, wherein step d, the material is ground to a particle size less than 30 μm.

51. The method according to claim 2, wherein step d, the material is ground to a particle size less than 20 μm.

52. The method according to claim 3, wherein step e, the refractive index in visible light that deviates by at most 10% from the refractive index of the binder phase when the binder phase is hydrated.

53. The method according to claim 3, wherein step e, the refractive index in visible light that deviates by at most 5% from the refractive index of the binder phase when the binder phase is hydrated.

54. The method according to claim 3, wherein step e, the additives are silicate glass.

* * * * *